United States Patent
Georgeson

(10) Patent No.: US 6,843,130 B2
(45) Date of Patent: Jan. 18, 2005

(54) SYSTEM AND METHOD FOR THE INSPECTION OF ADHESIVE

(75) Inventor: Gary E. Georgeson, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 33 days.

(21) Appl. No.: 10/308,975

(22) Filed: Dec. 3, 2002

(65) Prior Publication Data

US 2004/0103721 A1 Jun. 3, 2004

(51) Int. Cl.$^7$ .............................................. G01N 29/10
(52) U.S. Cl. .......................................... 73/600; 73/627
(58) Field of Search .......................... 73/597, 598, 599, 73/600, 602, 618, 620, 624, 627, 628, 629

(56) References Cited

U.S. PATENT DOCUMENTS

| | | | |
|---|---|---|---|
| 3,257,843 A | * | 6/1966 | Cowan ........................ 73/639 |
| 3,564,903 A | | 2/1971 | Woodmansee et al. |
| 3,813,926 A | * | 6/1974 | Stubbeman .................. 73/609 |
| 3,882,717 A | | 5/1975 | McCauley |
| 3,977,236 A | | 8/1976 | Raatz, Jr. et al. |
| 4,043,185 A | | 8/1977 | Siebert |
| 4,111,053 A | | 9/1978 | Geithman et al. |
| 4,117,733 A | | 10/1978 | Gugel |
| 4,122,724 A | | 10/1978 | Geithman et al. |
| 4,143,553 A | | 3/1979 | Martens et al. |
| 4,170,145 A | | 10/1979 | Kennedy et al. |
| 4,184,373 A | * | 1/1980 | Evans et al. .................. 73/588 |
| 4,244,227 A | | 1/1981 | Rudolph et al. |
| 4,487,071 A | | 12/1984 | Pagano et al. |
| 4,492,119 A | | 1/1985 | Dulapa et al. |
| 4,526,037 A | | 7/1985 | Wentzell et al. |
| 4,532,808 A | | 8/1985 | Wentzell et al. |
| 4,538,462 A | * | 9/1985 | Hartog et al. ................ 73/577 |
| 4,612,808 A | | 9/1986 | McKirdy et al. |
| 4,769,571 A | * | 9/1988 | Habeger et al. ............ 310/334 |
| 4,807,476 A | | 2/1989 | Cook et al. |
| 4,848,159 A | | 7/1989 | Kennedy et al. |
| 4,862,748 A | | 9/1989 | Woodmansee |
| 4,980,872 A | | 12/1990 | Oler et al. |
| 5,031,458 A | | 7/1991 | Young et al. |

(List continued on next page.)

FOREIGN PATENT DOCUMENTS

| | | | | |
|---|---|---|---|---|
| GB | | 1217597 | 12/1970 | |
| JP | | 2001021541 A | * 1/2001 | .......... G01N/29/10 |
| SU | | 1175738 A | 8/1985 | |
| SU | | 1721401 A1 | 3/1992 | |

OTHER PUBLICATIONS

B. Boro Djordjevic, Robert E. Green, Jr.; *Non–Contact Ultrasonic Techniques for Process Control of Composite Fabrication*; NDT net; Nov. 1997; pp. 1–8; vol. 2, No. 11; Conference on NDE applied to Composite Fabrication; St. Louis, Missouri; available at <http://www.ndt.net/article/aerol197/green/green.htm>.

(List continued on next page.)

Primary Examiner—Daniel S. Larkin
Assistant Examiner—Rose M. Miller
(74) Attorney, Agent, or Firm—Alston & Bird LLP

(57) ABSTRACT

A system for inspecting adhesive in a composite structure, such as for soft or improperly cured regions, includes a transducer and a processing element. The transducer can transmit a signal, such as an ultrasonic signal, into the adhesive such that at least a portion of the ultrasonic signal can propagate through the adhesive, reflect off of an interface between the adhesive and another material, and propagate back through the adhesive. Upon exiting the adhesive, then, the transducer can receive a reflected portion of the ultrasonic signal. Thereafter, the processing element can identify a defect, such as soft or improperly cured regions, in the adhesive upon a relationship of an amplitude of the reflected portion of the reflected ultrasonic signal to a predefined threshold.

23 Claims, 5 Drawing Sheets

U.S. PATENT DOCUMENTS

| | | | |
|---|---|---|---|
| 5,203,869 | A | 4/1993 | Bashyam |
| 5,249,457 | A | 10/1993 | Minichan |
| 5,438,402 | A | 8/1995 | Gupta |
| 5,586,155 | A | 12/1996 | Erbes et al. |
| 5,682,236 | A | 10/1997 | Trolinger et al. |
| 5,698,787 | A | 12/1997 | Parzuchowski et al. |
| 5,831,157 | A | 11/1998 | Woodmansee et al. |
| 5,902,935 | A | 5/1999 | Georgeson et al. |
| 5,938,875 | A | 8/1999 | Jessup et al. |
| 6,004,817 | A | 12/1999 | Chamberlain et al. |
| 6,018,999 | A | 2/2000 | Woodmansee et al. |
| 6,073,477 | A | 6/2000 | Woodmansee et al. |
| 6,168,358 | B1 | 1/2001 | Engwall et al. |
| 6,180,206 | B1 | 1/2001 | Kain, Jr. |
| 6,220,099 | B1 | 4/2001 | Marti et al. |
| 6,234,025 | B1 | 5/2001 | Gieske et al. |

OTHER PUBLICATIONS

Mahesh C. Bhardwaj; *High transduction Piezoelectric transducers and introduction of Non–Contact analysis; NDT net*; Jan. 2000; pp. 1–19; vol. 5, No. 01; available at <http://www.ndt.net/article/v05n01/bhardwaj/bhardwaj.htm>.

B. Boro Djordjevic; *Remote Non–Contact Ultrasonic Testing of Composite Materials*; pp. 1–6; available at <http://www.ndt.net/article/wcndt00/papers/idn358/ind358.htm> (visited Feb. 11, 2002).

QMI, Inc.; *Air–Coupled Ultrasonic Inspection; QMI*; pp. 1–3; available at <http://www.qmi–inc.com/AIRSCAN.htm> (visited Feb. 12, 2002).

QMI, Inc.; *SONDA 007CX—Multifrequency Instrument for Air–Coupled Ultrasonic Testing; QMI*; pp. 1–2; available at <http://www.qmi–inc.com/SONDA.htm> (visited Feb. 12, 2002).

QMI, Inc.; *The News\* Sonda–007CX—AIRSCAN®Digital Ultrasonic Air–Coupled Test Instrument* SONDA CX Airscan Ultrasonic Instrument; QMI; 2 pages; available at <http://www.qmi–inc.com/SONDA.htm> (visited Oct. 11, 2002).

B. Boro Djordjevic; *Remote Non–Contact Ultrasonic Testing of Composite Materials*; 6 pages; available at <http://www.ndt.net/article/wendt00/papres/idn358/idn358.htm> (visited Oct. 11, 2002).

S.N. Kolgatin, A.M. Stepanov, A.V. Khachatur'Yants; *Spall Damage to a Liquid Metal Accompanying Pulsed Action of Radiation*; UDC 532.595.2; 1985; pp. 702–707; Plenum Publishing Corporation.

G.N. Tret'Yachenko, L.I. Gracheva; *Thermal Deformation and Strength of Composite Materials at High Temperatures*; UDC 539.377:539.4; 1987; pp. 545–550; Plenum Publishing Corporation.

R.M. White; *Generation of Elastic Waves by Transient Surface Heating; Journal of Applied Physics*; 1963; pp. 3559–3567; vol. 34, No. 12.

Martin Veidt, Wolfgang Sachse; *Ultrasonic Evaluation of Thin, Fiber–Reinforced Laminates; Journal of Composite Materials*; 1994; pp. 329–342; vol. 28, No. 4; Technomic Publishing Co., Inc.

S.A. Novikov, A.I. Rusanov, I.R. Trunin, A. Ya, Uchaev; *Stress Wave Propagation and Fracture Processes in Metals During Rapid Bulk Heating; Strength of Materials*; 1994; pp. 137–140; vol. 26, No. 2; Plenum Publishing Corporation.

R.N. Wright, G.E. Korth, J.E. Flinn; *Particle Bonding, Annealing Response, and Mechanical Properties of Dynamically Consolidated Type 304 Stainless Steel Powders; Metallurgical Transactions*; 1989; pp. 2449–2457; vol. 20A.

\* cited by examiner

SYSTEM AND METHOD FOR THE INSPECTION OF ADHESIVE

FIELD OF THE INVENTION

The present invention relates generally to systems and methods for inspecting joints and, more particularly, to systems and methods for inspecting adhesive interconnecting elements of a composite structure utilizing a transducer.

BACKGROUND OF THE INVENTION

Composite parts have become commonly used throughout industry because of their engineering qualities, design flexibility and low weight. In particular, honeycomb composite structures having a honeycomb core bonded between two composite face sheets provide excellent strength and stiffness to weight ratios that make them particularly valued and widely used in the aerospace industry. Generally, composite structures, such as honeycomb composite structures, are made up of multiple elements. And often, these elements intersect and are interconnected by adhesive that is applied at the interconnection of the elements and thereafter cured to permanently join the elements. In this regard, the integrity of the adhesive at the interconnection of the elements is typically critical to the performance of the structure. For example, in the aircraft industry, the quality of adhesive at the intersection of elements in composite spars and co-cured structures are critical to their performance. Flaws such as cracks, voids, or porosity can form in the adhesive and adversely affect the composite structure. In addition, flaws such as regions of inadequately cured adhesive can also adversely affect the composite structure.

To help ensure the integrity of adhesive interconnecting elements in composite structures, the adhesive is generally inspected for flaws. Such adhesive may not always be adequately inspected, however, particularly using traditional nondestructive inspection (NDI) methods. For example, one NDI method of inspecting adhesive joining elements of a composite structure includes using a hand-operated durometer that can measure the hardness near the surface of exposed adhesive. And while using a durometer to measure the hardness of the adhesive near the surface of the exposed adhesive can adequately detect flaws near the surface of the adhesive, many flaws exist well below the surface of the adhesive. Thus, such flaws are undetectable using conventional methods such as those utilizing a durometer.

SUMMARY OF THE INVENTION

In light of the foregoing background, an improved system and method are provided for inspecting adhesive in a composite structure. As such, the system and method of embodiments of the present invention can reliably detect defects within the adhesive between elements of a composite structure. The system and method of embodiments of the present invention therefore reliably detect defects within the adhesive, while overcoming the drawbacks of other inspection methods. In this regard, embodiments of the system and method can inspect the adhesive without the use of couplants that could contaminate the composite structure. The system and method of embodiments of the present invention can also detect flaws below the surface of the adhesive, in contrast to methods utilizing a durometer. Further, the system of the present invention can be implemented without requiring equipment on multiple sides of the composite structure and, as such, adhesive in composite structures such as honeycomb sandwich panels can be inspected during fabrication of the panels, such as while the panels lie on a lay-up tool.

Typically, a composite structure such as a honeycomb sandwich panel includes at least two sections separated from one another to thereby define a gap. Disposed within the gap, then, the composite structure includes adhesive to thereby bond the sections. The system and method of embodiments of the present invention are therefore designed to reliably detect defects in the adhesive, such as defects indicative of voids, cracks and/or regions of inadequately cured adhesive.

According to one aspect of the present invention, a system is provided for inspecting adhesive in the composite structure. The system includes a transducer and a processing element. The transducer is disposed proximate the adhesive. In this regard, the transducer can include at least one rubber sheet disposed proximate a face of the transducer between the transducer and the adhesive such that the rubber sheets can solid-couple the transducer to the adhesive. Alternatively, the transducer can be within a wheel probe. In such an embodiment, the wheel probe includes a rubber strip capable of solid-coupling the transducer to the adhesive.

The transducer can transmit a signal, such as an ultrasonic signal, into the adhesive such that at least a portion of the signal can propagate through the adhesive and reflect back through the adhesive. Upon exiting the adhesive, then, the transducer can receive the reflected portion of the signal. Once the transducer has received the reflected portion of the signal, the processing element is capable of identifying a defect in the composite structure based upon: (a) an amplitude of the reflected portion of the signal received by the transducer, and/or (b) a transit time between transmission of the signal and reception of the reflected portion of the signal.

More particularly, the processing element is capable of identifying a defect based upon a comparison of the amplitude of the reflected portion of the signal and a predefined threshold, where the predetermined threshold is based upon the amplitude of the signal transmitted by said transducer. In this regard, the processing element is capable of identifying a defect, such as at least one region of incompletely cured adhesive, when the amplitude of the reflected portion of the signal is less than a predetermined percentage of the amplitude of the signal transmitted by the transducer. Additionally, or alternatively, the processing element can be capable of identifying a defect, such as a void, when the transit time is less than a predetermined time.

The system can also include a scanning assembly electrically connected to the processing element. In such embodiments, the transducer is secured to the scanning assembly such that the scanning assembly can guide the transducer along the adhesive. In this regard, the transducer can be capable of repeatedly transmitting signals into the adhesive at different points therealong, and capable of receiving the reflected portion at each point. In these embodiments, the processing element can identify a defect at each point based upon: (a) an amplitude of the reflected portion of the signal received at the respective point, and/or (b) the transit time.

A method of inspecting adhesive in a composite structure is also provided.

BRIEF DESCRIPTION OF THE DRAWINGS

Figure 1:
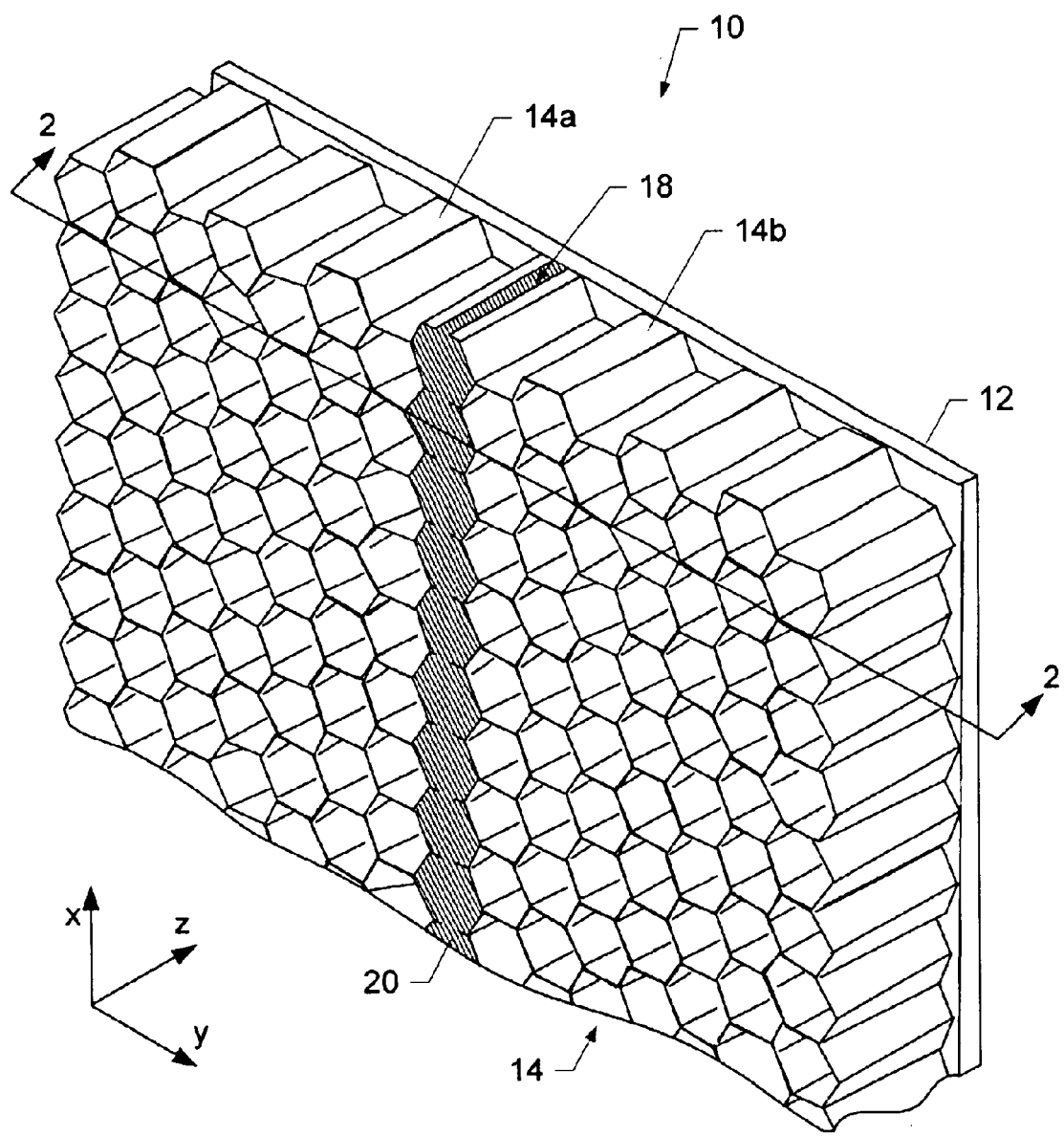
Figure 2:
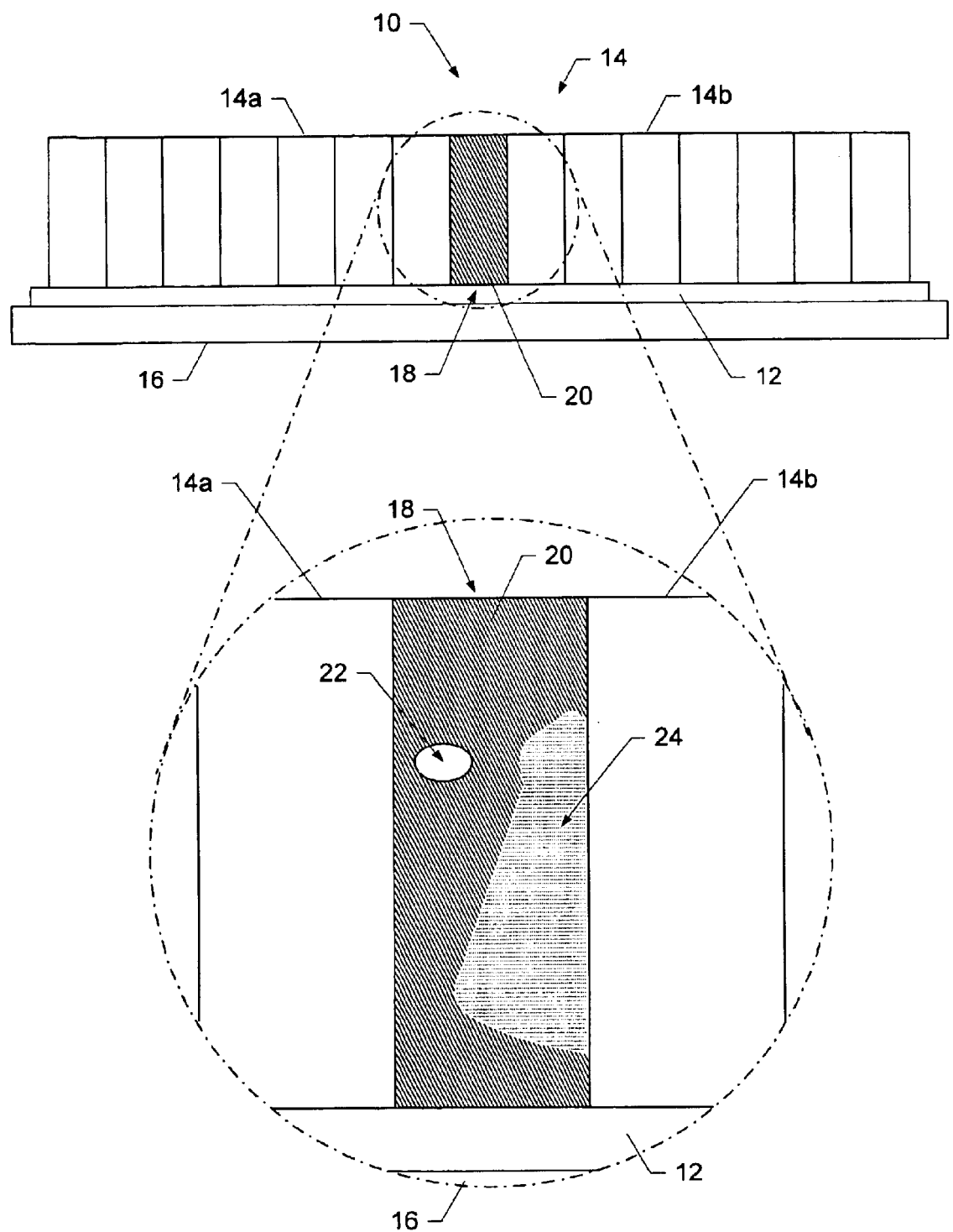
Figure 3:
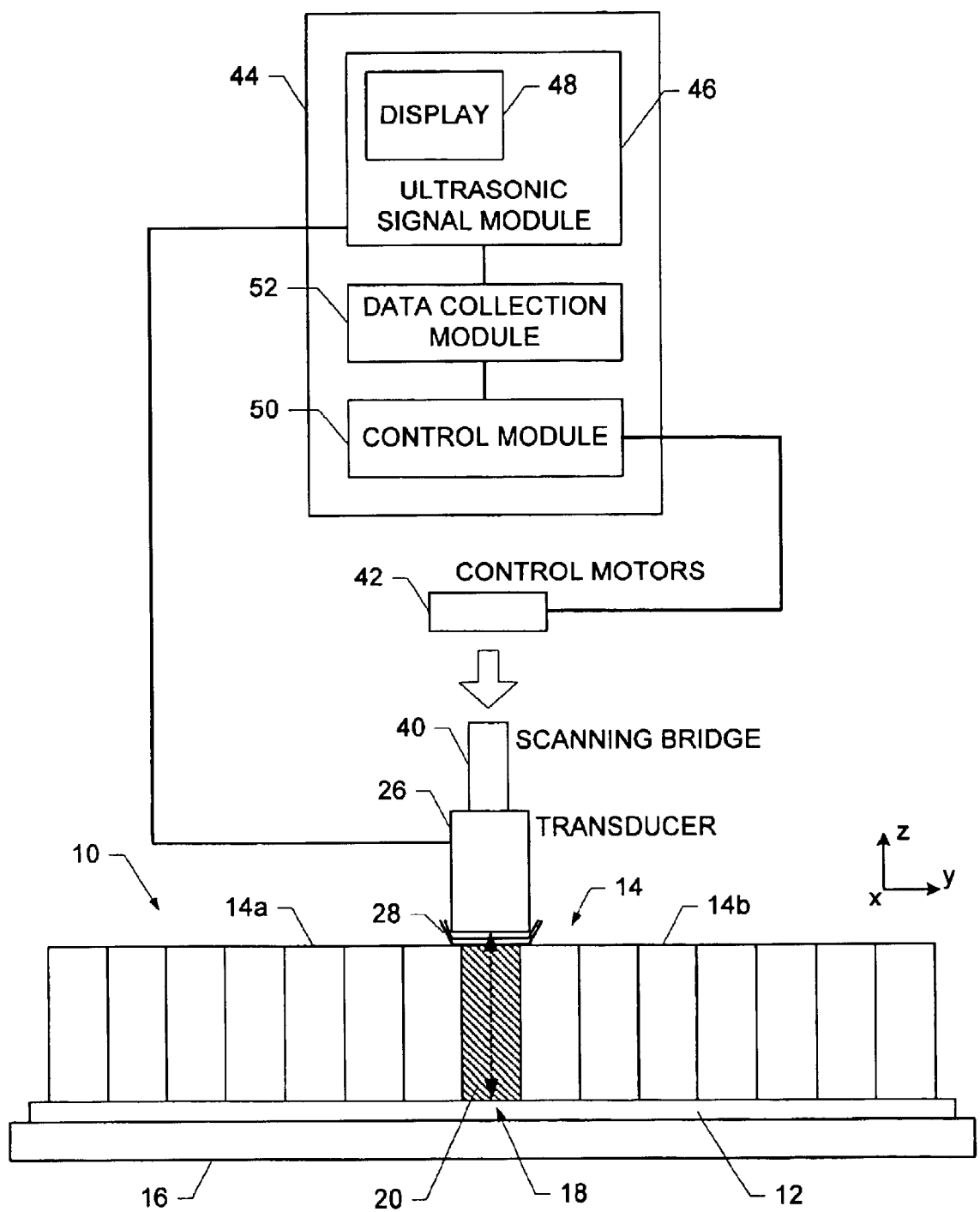
Figure 4A:
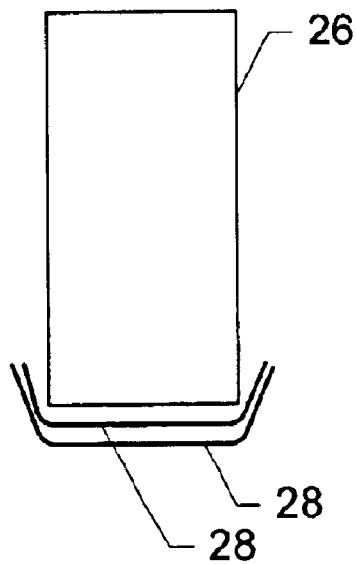
Figure 4B:
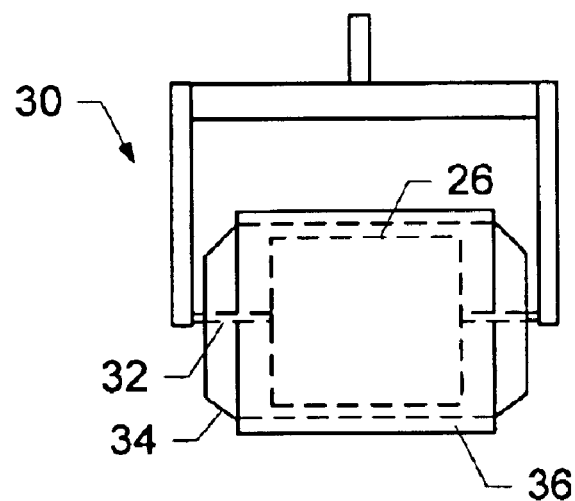
Figure 5A:
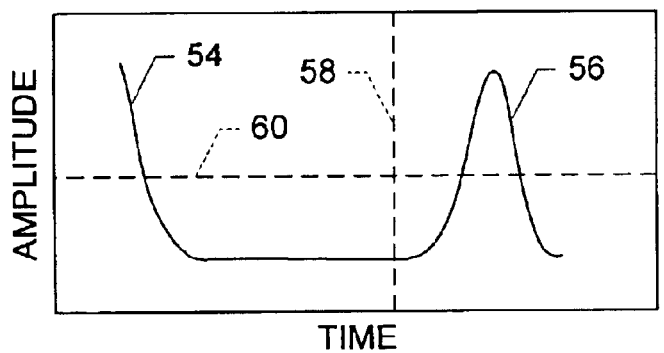
Figure 5B:
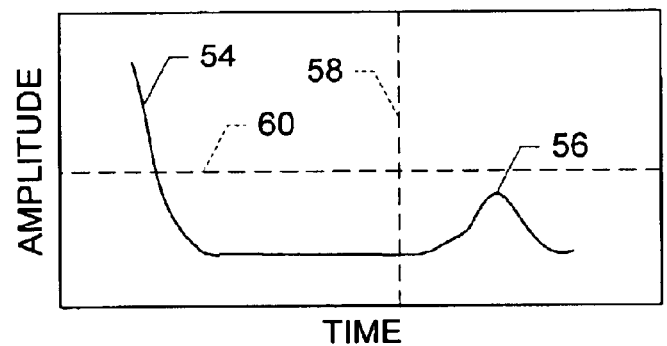
Figure 5C:
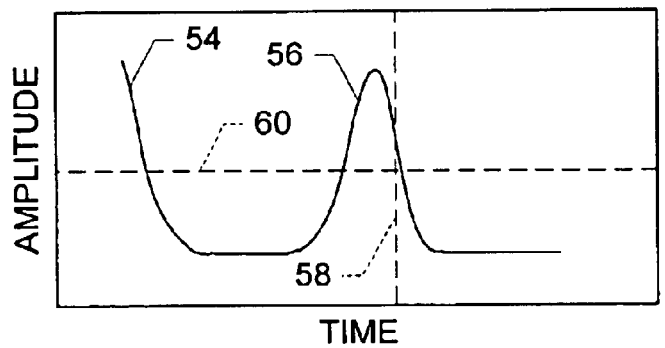

Having thus described the invention in general terms, reference will now be made to the accompanying drawings, which are not necessarily drawn to scale, and wherein:

FIG. 1 is a perspective view of a honeycomb composite structure including adhesive for inspection according to one embodiment of the present invention;

FIG. 2 is a cross-sectional view of the composite structure of FIG. 1 taken along line 2—2, where the composite structure is situated on a lay-up tool with an exploded inset of the adhesive including various defects that can appear in the adhesive;

FIG. 3 is a schematic block diagram of a system for inspecting adhesive in a composite structure according to one embodiment of the present invention;

FIGS. 4A and 4B illustrate various configurations of transducers capable of operating within the system of according to one embodiment of the present invention; and FIGS. 5A, 5B and 5C illustrate various plots of a transmitted ultrasonic signal and a received, reflected ultrasonic signal at different points along the length of the adhesive, according to one embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

A system and method are provided for inspecting adhesive at an interconnection between two elements of a composite structure. The composite structure will be shown and described as a composite honeycomb sandwich panel. It should be understood, however, that the composite structure can comprise any of a number of different composite structures that include at least two elements interconnected by adhesive.

Referring to FIGS. 1 and 2, there is shown a composite honeycomb sandwich panel structure generally indicated at 10. The honeycomb sandwich panel generally has outer face sheets or skins, one of which, referred to as a tool-side skin 12, is shown. The outer skins are adhered to a central honeycomb core 14. The finished skins typically comprise laminates of layers of fiber-reinforced organic matrix resin (prepregs) in a cured and consolidated composite form. The core can comprise any of a number of different materials such as, for example, paper, synthetic paper (e.g., NOMEX brand paper manufactured by E. I. duPont de Nemours and Company of Wilmington, Del.), metal, composite, fiberglass, or the like, as appropriate for the application.

According to one conventional fabrication technique, the tool-side skin 12 is laid up on the surface of a lay-up tool, sometimes referred to as a "bond assembly jig" or BAJ 16 (a portion of which is shown in FIG. 2). The honeycomb core 14 can then be cut and fitted onto the tool-side skin. In this regard, the honeycomb core typically comprises at least two sections of honeycomb core, two of which are shown and designated 14a, 14b. The sections of honeycomb core are separated by a gap 18, which typically varies in length between a quarter inch and three-eighths of an inch. To connect, bond or otherwise splice the two sections of the core together, then, an adhesive 20 is typically disposed within the gap. The adhesive can comprise any of a number of different adhesives, both room-temperature cured and heat cured. For example, the adhesive can comprise a foaming adhesive such as model 899-55 REDUX node bond adhesive manufactured by Hexcel Composites, a subsidiary of the Hexcel Corporation of Dublin, Calif.

After the honeycomb core sections 14a, 14b have been fitted onto the tool-side skin 12 and the adhesive 20 disposed between the core sections, the tool-side skin and core assembly can be covered with a vacuum bag from which the air is withdrawn with a vacuum source. The bagged assembly can then be inserted into an autoclave and reconnected to the vacuum source such that additional air, if any, can be withdrawn while the bagged assembly is being heated to cure the resin in the tool-side skin to bond the core to the skin, and to cure the adhesive to bond the core sections together. Then, the bagged assembly can be removed from the autoclave and unbagged.

The honeycomb core 14 assembly can then be machined to the desired configuration. Typically, the assembly is machined by a computer numerical controlled (CNC) machine tool such as a gantry mounted robot. However, because it is typically not possible to perform this machining operation with the assembly on the BAJ, the assembly can be broken out of the BAJ 16, and transferred to another tool known as a "bond mill fixture" or BMF (not shown). In this regard, the BMF has a part support surface designed to have the same profile as the BAJ and also includes vacuum ports and hold down mechanisms intended to hold the assembly in place on the BMF while the honeycomb core is machined to sculpt it to the desired shape The BMF also had index features for accurately locating it on the machine tool bed of the CNC machine tool, and it has an accurately machined "A" datum plane for orienting the part support surface of the BMF relative to the machine tool bed to facilitate accurate machining by CNC machine tools.

The partially fabricated honeycomb sandwich panel 10 can then be removed from the BMF and the honeycomb core 14 and cleaned to remove dust from the cells. The cleaned panel can then be repositioned onto the BAJ 16 where it is reattached with clamps and hold-down devices. The second skin, known as a bag-side skin (not shown) can then be laid over the honeycomb core and covered with another vacuum bag. To bond the bag-side skin to the core, then, the BAJ can be reinserted back into the autoclave. After curing, the cured part can again be removed from the BAJ and repositioned back onto the BMF for final trim, if necessary.

As shown in the exploded inset portion of FIG. 2, various defects can appear in the adhesive 20 within the gap 18 defined between the honeycomb core sections 14a, 14b that affect performance of the honeycomb sandwich panel 10. For example, the adhesive can include defects such as voids 22 and/or cracks (not shown). Additionally, or alternatively, the adhesive can include one or more regions 24 of inadequately, or incompletely, cured adhesive (sometimes referred to as "soft" adhesive). In this regard, now referring to FIG. 3, the present invention provides a system and method to inspect the adhesive 20 for such defects. To inspect the adhesive, the system includes a transducer 26 that is capable of transmitting signals into the adhesive and receiving reflected signals from the adhesive, respectively. In this regard, defects in the joint can be identified based upon a relationship between the transmitted and reflected ultrasonic signals, as described below.

The transducer 26 can comprise any of a number of different types of transducers capable of functioning in accordance with the present invention. In one advantageous embodiment, the transducer is an ultrasonic testing (UT) transducer capable of transmitting and receiving ultrasonic signals. The transducer is adapted to be solid-coupled to the adhesive 20 and, therefore, does not require a liquid couplant like many conventional transducers. In this regard, the system can inspect the adhesive of composite structures that might otherwise be contaminated by a liquid couplant. The transducer can comprise any of a number of different UT transducers capable of being solid-coupled to the adhesive.

As shown schematically in FIG. 4A, the transducer 26 can comprise a conventional transducer that includes one or more sheets 28, such as rubber sheets, stretched over the face of the transducer. In such an embodiment, for example, the transducer can comprise an F-Style 5 MHz gamma series 224-000 model transducer manufactured by Krautkramer Ultrasonic Systems, a subsidiary of the Agfa-Gevaert Group of Mortsel, Belgium. Alternatively, as shown in FIG. 4B, the transducer can be mounted within a wheel probe 30. Such a wheel probe may have an axle 32, to which the transducer is mounted, and a rotor 34 (i.e., wheel), which rotates about the axle on bearings. A replaceable strip 36, such as a rubber strip, can then fit around the rotor to provide UT coupling between the transducer and the adhesive. One example of such a wheel probe is an SSW wheel probe manufactured by Sigma Instruments Corporation of Kennewick, Wash.

By including a sheet or strip, such as a rubber sheet or strip, between the transducer and the adhesive and applying slight pressure on the transducer toward the adhesive, the sheet or strip can seal against the surface of the adhesive and allow most of the signals from the transducer to pass into the adhesive unimpeded. Without the sheet or strip, an air gap can be created between the transducer and the adhesive because the transducer does not typically conform and seal to the adhesive, particularly as the adhesive is not perfectly flat, nor perfectly smooth. Such a gap, then, can produce a large impedance mismatch for the signals from the transducer.

To inspect all of the adhesive 20, the transducer 26 can be guided over the adhesive along the entire length of the gap 18 between the honeycomb core sections 14a, 14b. The transducer can be guided over the adhesive in any one of a number of different manners, including by hand. In one advantageous embodiment, however, the system includes a scanning assembly to guide the transducer over the adhesive. Referring again to FIG. 3, the scanning assembly includes a guide assembly capable of moving the transducer relative to the gap. The guide assembly can comprise any of a number of different elements. For example, the guide assembly can comprise a robotic scanning bridge 40 operated by various control motors 42, such as any of a number of gantry robots controlled by a Cimroc model controller, both manufactured by PaR Systems, Inc. of Shoreview, Minn. In this regard, the scanning bridge preferably moves the transducer longitudinally along an "x" axis parallel to the length of the gap to inspect along the length of the adhesive.

Regardless of the matter in which the transducer 26 is guided along the length of the adhesive 20, the system includes a processing element 44 to identify defects in the adhesive during inspection. Generally the processing element includes an ultrasonic signal module 46 capable of providing electrical pulses to the transducer 26, which transmits the ultrasonic signals therefrom. Also, the ultrasonic signal module is capable of receiving electrical pulses from the receiving transmitter, which generates the electrical pulses from the reflected ultrasonic signals received by the transducer. Further, the signal module can include a display 48, such as a screen, monitor or the like, for displaying the electrical signals provided to and received from the transducer.

In addition to the ultrasonic signal module 46, in embodiments where the transducer 26 is guided by the scanning assembly, the processing element 44 generally includes a control module 50 for controlling the movement of the scanning bridge 40 and, thus, the transducer 26. If so desired, the processing element can also include a data collection module 52 capable of recording and thereafter storing data representative of the amplitudes of the transmitted ultrasonic signals and the reflected ultrasonic signals received by the transducer. The ultrasonic signal module, control module and data collection module of the processing element can each include separate elements, or one or more of the modules can be embodied in a single device, such as a personal computer, high level processor or the like. For example, in one embodiment, the ultrasonic signal module can comprise an ultrasonic inspection instrument, such as a USN 52L model Ultrasonic Flaw Detector, manufactured by Krautkramer Ultrasonic Systems. Also, for example, the control module and data collection module can collectively be embodied in a personal computer capable of performing the functions of both modules, with the ultrasonic signal module embodied by another processing element.

The adhesive 20 can be inspected at any one of a number of different times during fabrication of the composite structure. In embodiments where the composite structure comprises a honeycomb sandwich panel 10, however, the adhesive is preferably inspected after removing the bagged tool-side skin 12 and honeycomb core 14 assembly from the autoclave and unbagging the tool-side skin and core assembly, and before laying the bag-side skin over the core. In operation, then, according to one embodiment, the adhesive of a composite structure is inspected by first setting the transducer 26 relative to the adhesive 20. In this regard, the transducer is set proximate a first end of the adhesive so that the transducer is solid-coupled to the adhesive, such as by one or more sheets 28 stretched over the face of the transducer, or by a replaceable strip 36 (in instances in which the transducer is mounted within a wheel probe 30). Additionally, the transducer is preferably positioned such that the axis of transmission of the transducer intersects the adhesive at a first predetermined point at one end of the adhesive (along the "x" axis).

Once the transducer 26 is positioned, the ultrasonic signal module 46 can direct the transducer to transmit an ultrasonic signal into the adhesive 20. Upon entering the adhesive, the ultrasonic signal propagates through adhesive to an intersection of the adhesive (or more, particularly, a second end of the adhesive) and the tool-side skin 12 where at least a portion (typically a significant portion) of the ultrasonic signal reflects off of the tool-side skin (with the remaining portion propagating through the tool-side skin). The ultrasonic signal typically transmitted by the transducer is a longitudinal mode signal, however, at different angles at which the ultrasonic signal reflects off of the interface of the adhesive and the tool-side skin, portions of the ultrasonic signal can undergo a mode conversion into a shear (i.e., transverse) mode signal. In this regard, the ultrasonic signal reflected off the interface of the adhesive and tool-side skin typically utilized by the system is the reflected longitudinal mode ultrasonic signal.

The reflected ultrasonic signal then propagates back through the adhesive 20, exiting the adhesive at the first end. Upon exiting the adhesive, then, the transducer 26 receives the reflected portion of the ultrasonic signal. As the transducer transmits and receives the ultrasonic signal and reflected ultrasonic signals, respectively, the data collection module 52 can record and/or save data representative the transmitted ultrasonic signals and the reflected ultrasonic signals. Additionally, the data collection module can record and/or save the position of the transducer relative to the adhesive.

After the transducer 26 transmits the ultrasonic signal and receives any reflected portion of the ultrasonic signal, the control module 50 can move the transducer lengthwise an incremental amount along the length of the adhesive 20 (along the "x" axis) such that the axis of transmission of the transducer intersects the adhesive at another point. For example, for adhesive that has a length of 120 inches, the control module can move the transducer 0.03 to 0.05 inches along the length. The control module can move the transducer in other increments if desired, however, such as depending upon the desired resolution. The adhesive typically follows a linear path within the gap 18, however, it should be understood that the adhesive can have a non-linear path without departing from the spirit and scope of the present invention.

Once the transducer has been moved, the ultrasonic signal module 46 directs the transducer to transmit another ultrasonic signal into the adhesive. The ultrasonic signal will again propagate through the adhesive and exit the adhesive back into the transducer. Also as before, the data collection module 52 can record and/or save data representative the transmitted ultrasonic signals and the reflected ultrasonic signals. Additionally, the data collection module can record and/or save the position of the transducer relative to the adhesive, such as the position of the transducer along the length of the adhesive. The control module repeatedly moves the transducer along the length, with the transducer transmitting ultrasonic signals and receiving reflected portions of the ultrasonic signals, respectively. And the data collection module records and/or saves respective data at each point. By transmitting/receiving the ultrasonic signals, recording the data and moving the transducer, the system can scan the length of the adhesive.

At each point along the length of the adhesive 20, flaws in the adhesive can be determined based upon a relationship between the transmitted ultrasonic signal and the received ultrasonic signal. In a non-defective portion of the adhesive, the transducer 26 will receive a reflected ultrasonic signal having an amplitude above a predefined threshold, with the reflected ultrasonic signal being received at least a predetermined time after the transducer transmits the ultrasonic signal. If the transducer transmits an ultrasonic signal into a portion of the adhesive including a void 22, crack or similar flaw including a lack or absence of adhesive, however, a significant portion of the ultrasonic signal will reflect from the interface between the adhesive and the flaw and, as such, not continue to propagate through the adhesive to the interface of the adhesive and the tool-side skin 12. As such, the time between when the transducer transmits the ultrasonic signal and receives the reflected ultrasonic signal will be shorter than the predetermined time. Additionally, or alternatively, if the transducer transmits an ultrasonic signal into a portion of the adhesive including one or more regions 24 of inadequately cured adhesive or similar flaw, at least a portion of the ultrasonic signal will be attenuated by the flaw. Thus, the amplitude of the reflected ultrasonic signal will be below the predefined threshold although the timing will be similar to a signal transmitted through an adhesive without such flaws.

The predefined threshold can be defined in any one of a number of different manners but, in one embodiment, the threshold is defined based upon the amplitude of the ultrasonic signal transmitted by the transducer 26. For example, the threshold can be defined to equal half of the amplitude of the ultrasonic signal transmitted. Thus, if the transducer receives a reflected ultrasonic signal more than half the transmitted signal, the respective portion of the adhesive is deemed not defective. But if the transducer receives a reflected ultrasonic signal less than half the transmitted signal, the respective portion is identified as defective. Alternatively, for example, the threshold can be defined based upon the amplitude of a reflected portion of an ultrasonic signal transmitted through a known non-defective adhesive of the same or similar type as the adhesive being inspected, and having the same width as the adhesive being inspected (along the "z" axis). For example, the threshold can be defined to equal less than, such as 25% less than, the amplitude of a reflected portion of an ultrasonic signal transmitted through such a known non-defective adhesive.

The predetermined time can similarly be defined in any one of a number of different manners. In one embodiment, for example, the predetermined time is defined based upon the time required for an ultrasonic signal to propagate entirely through, reflect back and return through a known non-defective adhesive of the same or similar type as the adhesive being inspected, and having the same width as the adhesive being inspected (along the "z" axis). For example, the predetermined time can be defined to be slightly less, such as 5% less, than the time required for an ultrasonic signal to propagate entirely through, reflect back and return through the known non-defective adhesive.

To facilitate detecting the defects at each position, the data collected by the data collection module 52 representative of the reflected ultrasonic signals received by the transducer 26 can be used to plot the reflected ultrasonic signal along with the transmitted ultrasonic signal, both as a function of the time the transducer transmits the ultrasonic signal and receives the reflected ultrasonic signal, respectively. The plot, in turn, can be presented to a user, such as via the display 48 of the signal module 46. Alternatively, the plot or an electronic representation thereof may be automatically analyzed, such as by the processing element 44. Thus, FIGS. 5A, 5B and 5C, illustrate various plots of the transmitted ultrasonic signal (designated 54) and the received, reflected ultrasonic signal (designated 56) at different points along the length of the adhesive, which can be presented by the display of the signal module. For comparison purposes, the display can, but need not, also depict the predetermined time (designated 58) and/or the predefined threshold (designated 60).

The plot shown in FIG. 5A represents a scenario wherein the transducer 26 receives the reflected ultrasonic signal 56 at a time after the predetermined time 58. Additionally, the reflected ultrasonic signal has an amplitude above the predefined threshold 60. Therefore, the adhesive 20 at the point reflected in the plot of FIG. 5A can be deemed non-defective. As illustrated by the plot in FIG. 5B, in another scenario, the transducer receives the reflected ultrasonic signal at a time after the predetermined time. However, the reflected ultrasonic signal has an amplitude below the predefined threshold. As such, the adhesive at the point on the adhesive reflected in the plot of FIG. 5B can be deemed defective, with the flaw characterized as one or more regions 24 of inadequately, or incompletely, cured adhesive or the like. In yet another scenario, represented by the plot illustrated in FIG. 5C, the reflected ultrasonic signal has an amplitude above the threshold. The adhesive at the point reflected in the plot of FIG. 5C is deemed defective, however, as the transducer receives the reflected ultrasonic signal at a time before the predetermined time. In such instances, the flaw can be characterized as a void 22, crack or the like.

The system and method of embodiments of the present invention therefore reliably detect defects within the adhesive 20, while overcoming the drawbacks of other inspection methods. In this regard, embodiments of the system and method can inspect the joint without the use of couplants that could contaminate the composite structure. The system and method of embodiments of the present invention can also detect flaws below the surface of the adhesive, in contrast to methods utilizing a durometer. Further, the system of the present invention can be implemented without requiring equipment on multiple sides of the composite structure and, as such, adhesive in composite structures such as honeycomb sandwich panels can be inspected while the panel lies on a BAJ.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A system for inspecting adhesive bonding together a plurality of elements in a composite structure that includes sections spaced apart to thereby define a gap, wherein the composite structure further includes at least partially cured adhesive disposed within the gap to thereby connect the sections, said system comprising:
    a transducer capable of transmitting a signal directly into the adhesive such that at least a portion of the signal can propagate through the adhesive, reflect back through the adhesive and be received by said transducer; and
    a processing element capable of identifying at least one region of incompletely cured adhesive in the composite structure based upon an amplitude of the reflected portion of the signal received by said transducer.

2. A system according to claim 1, wherein said processing element is capable of responding to a decrease in the amplitude of the signal transmitted by said transducer by a predetermined amount.

3. A system according to claim 1, wherein said processing element is further capable of identifying a defect in the composite structure based upon a relationship of a transit time between transmission of the signal and reception of the reflected portion of the signal to a predetermined time.

4. A system according to claim 3, wherein said processing element is capable of identifying a defect when the transit time is less than the predetermined time.

5. A system according to claim 4, wherein said processing element is capable of identifying a void defined within the adhesive when the transit time is less than the predetermined time.

6. A system according to claim 1 further comprising a scanning assembly electrically connected to said processing element, wherein said transducer is carried by said scanning assembly such that said scanning assembly guides said transducer along the adhesive.

7. A system according to claim 1, wherein said transducer is capable of repeatedly transmitting signals into the adhesive at different points therealong, and capable of receiving the reflected portion at each point, and wherein said processing element is capable of identifying at least one region of incompletely cured adhesive at each point based upon an amplitude of the reflected portion of the signal received at the respective point.

8. A system according to claim 7, wherein said processing element is further capable of identifying a defect as each point based upon a relationship of a transit time between transmission of the signal and reception of the reflected portion of the signal to a predetermined time.

9. A system for inspecting adhesive bonding together a plurality of elements in a composite structure that includes sections spaced apart to thereby define a gap, wherein the composite structure further includes at least partially cured adhesive disposed within the gap to thereby connect the sections, said system comprising:
    a transducer capable of transmitting a signal into the adhesive such that at least a portion of the signal can propagate through the adhesive, reflect back through the adhesive and be received by said transducer, wherein said transducer includes at least one rubber sheet disposed proximate a face of said transducer between said transducer and the adhesive, and wherein the at least one rubber sheet is capable of solid-coupling said transducer to the adhesive; and
    a processing element capable of identifying at least one region of incompletely cured adhesive in the composite structure based upon an amplitude of the reflected portion of the signal received by said transducer.

10. A system for inspecting adhesive bonding together a plurality of elements in a composite structure that includes sections spaced apart to thereby define a gap, wherein the composite structure further includes at least partially cured adhesive disposed within the gap to thereby connect the sections, said system comprising:
    a transducer capable of transmitting a signal into the adhesive such that at least a portion of the signal can propagate through the adhesive, reflect back through the adhesive and be received by said transducer;
    a wheel probe with said transducer therein, wherein said wheel probe includes a rubber strip capable of solid-coupling said transducer to the adhesive; and
    a processing element capable of identifying at least one region of incompletely cured adhesive in the composite structure based upon an amplitude of the reflected portion of the signal received by said transducer.

11. A system for inspecting adhesive bonding together a plurality of elements in a composite structure that includes sections spaced apart to thereby define a gap, wherein the composite structure further includes at least partially cured adhesive disposed within the gap to thereby connect the sections, said system comprising:
    a transducer capable of transmitting a signal into the adhesive such that at least a portion of the signal can propagate through the adhesive, reflect back through the adhesive and be received by said transducer; and
    a processing element capable of identifying at least one region of incompletely cured adhesive in the composite structure based upon an amplitude of the reflected portion of the signal received by said transducer, wherein said processing element is capable of identifying at least one region of incompletely cured adhesive based upon a comparison of the amplitude of the reflected portion of the signal and a predefined threshold, and wherein the predetermined threshold is based upon the amplitude of the signal transmitted by said transducer.

12. A method for inspecting a joint in a composite structure comprising:
    providing a composite structure that includes sections spaced apart to thereby define a gap, wherein the composite structure further includes at least partially cured adhesive disposed within the gap to thereby connect the sections;

transmitting a signal directly into the adhesive such that at least a portion of the signal can propagate through the adhesive and reflect back through the adhesive;

receiving a reflected portion of the signal; and identifying at least one region of incompletely cured adhesive in the composite structure based upon an amplitude of the reflected portion of the signal.

13. A method according to claim 12, wherein transmitting a signal comprises repeatedly transmitting signals into the adhesive at different points therealong, wherein receiving the reflected portion occurs for each point, wherein identifying at least one region of incompletely cured adhesive comprises identifying at least one region of incompletely cured adhesive at each point based upon an amplitude of the reflected portion of the signal received at the respective point.

14. A method according to claim 13 further comprising identifying a defect at each point based upon a transit time between transmission of the signal and reception of the reflected portion of the signal relative to a predetermined time.

15. A method for inspecting a joint in a composite structure comprising:

providing a composite structure that includes sections spaced apart to thereby define a gap, wherein the composite structure further includes at least partially cured adhesive disposed within the gap to thereby connect the sections;

transmitting a signal into the adhesive such that at least a portion of the signal can propagate through the adhesive and reflect back through the adhesive;

receiving a reflected portion of the signal; and identifying at least one region of incompletely cured adhesive in the composite structure based upon an amplitude of the reflected portion of the signal, wherein identifying at least one region of incompletely cured adhesive comprises identifying at least one region of incompletely cured adhesive based upon a comparison of the amplitude of the reflected portion of the signal and a predefined threshold, and wherein the predetermined threshold is based upon the amplitude of the transmitted signal.

16. A method according to claim 15, wherein identifying at least one region of incompletely cured adhesive comprises identifying at least one region of incompletely cured adhesive when the amplitude of the reflected portion of the signal is less than a predetermined percentage of the amplitude of the transmitted signal.

17. A method according to claim 16, further comprising identifying a defect based upon a transit time between transmission of the signal and reception of the reflected portion of the signal to a predetermined time.

18. A method according to claim 17, wherein identifying a defect in the composite structure based upon a relationship of a transit time comprises identifying a defect when the transit time is less than the predetermined time.

19. A method according to claim 18, wherein identifying a defect when the transit time is less than the predetermined time comprises identifying a void defined within the adhesive when the transit time is less than the predetermined time.

20. A method for inspecting a joint in a composite structure comprising:

providing a composite structure that includes sections spaced apart to thereby define a gap, wherein the composite structure further includes at least partially cured adhesive disposed within the gap to thereby bond the sections;

transmitting a signal directly into the adhesive such that at least a portion of the signal can propagate through the adhesive and reflects back through the adhesive;

receiving a reflected portion of the signal; and separately identifying at least one of a region of incompletely cured adhesive and a void within the adhesive, wherein at least one of the region and the void are identified based upon the reflected portion of the signal.

21. A method according to claim 20, wherein identifying a void within the adhesive comprises identifying a void within the adhesive when the transit time is less than the predetermined time.

22. A method for inspecting a joint in a composite structure comprising;

providing a composite structure that includes sections spaced apart to thereby define a gap, wherein the composite structure further includes at least partially cured adhesive disposed within the gap to thereby bond the sections;

transmitting a signal into the adhesive such that at least a portion of the signal can propagate through the adhesive and reflects back through the adhesive;

receiving a reflected portion of the signal; and separately identifying at least one of a region of incompletely cured adhesive and a void within the adhesive, wherein at least one of the region and the void are identified based upon the reflected portion of the signal, wherein identifying a region of incompletely cured adhesive comprises identifying a region of incompletely cured adhesive based upon a comparison of the amplitude of the reflected portion of the signal and a predefined threshold, and wherein the predetermined threshold is based upon the amplitude of the transmitted signal.

23. A method according to claim 22, wherein identifying a region of incompletely cured adhesive comprises, identifying a region of incompletely cured adhesive when the amplitude of the reflected portion of the signal is less than a predetermined percentage of the amplitude of the transmitted signal.

* * * * *